US009226696B2

(12) United States Patent
Kiani

(10) Patent No.: US 9,226,696 B2
(45) Date of Patent: Jan. 5, 2016

(54) PATIENT SAFETY SYSTEM WITH AUTOMATICALLY ADJUSTING BED

(71) Applicant: MASIMO CORPORATION, Irvine, CA (US)

(72) Inventor: Massi Joe E. Kiani, Laguna Niguel, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 14/275,090

(22) Filed: May 12, 2014

(65) Prior Publication Data

US 2014/0333440 A1 Nov. 13, 2014

Related U.S. Application Data

(63) Continuation of application No. 13/277,145, filed on Oct. 19, 2011, now Pat. No. 8,723,677.

(60) Provisional application No. 61/405,097, filed on Oct. 20, 2010.

(51) Int. Cl.
| | |
|---|---|
| *G08B 23/00* | (2006.01) |
| *A61B 5/11* | (2006.01) |
| *G08B 21/22* | (2006.01) |
| *A61B 5/00* | (2006.01) |
| *A47C 21/08* | (2006.01) |
| *A61G 7/012* | (2006.01) |
| *G08B 21/02* | (2006.01) |
| *A61G 7/05* | (2006.01) |

(52) U.S. Cl.
CPC .............. *A61B 5/1115* (2013.01); *A47C 21/08* (2013.01); *A61B 5/6892* (2013.01); *A61G 7/012* (2013.01); *A61G 7/0506* (2013.01); *A61G 7/0507* (2013.01); *G08B 21/02* (2013.01); *G08B 21/22* (2013.01); *A61B 5/002* (2013.01); *A61B 2505/00* (2013.01); *A61G 2007/0509* (2013.01); *A61G 2007/0515* (2013.01)

(58) Field of Classification Search
CPC ...................................... A61B 5/1115
USPC ............................ 340/573.4, 573.7
See application file for complete search history.

(56) References Cited

U.S. PATENT DOCUMENTS

| | | | |
|---|---|---|---|
| 4,907,845 A * | 3/1990 | Wood | 340/573.4 |
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,163,438 A | 11/1992 | Gordon et al. | |
| 5,319,355 A | 6/1994 | Russek | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |

(Continued)

*Primary Examiner* — Kerri McNally
(74) *Attorney, Agent, or Firm* — Knobbe Martens Olson & Bear LLP

(57) ABSTRACT

A patient safety system including an adjustable bed and a patient monitoring system is disclosed herein. The adjustable bed can automatically adjust to a safe default configuration when the safety system detects that a care provider has left the patient's room or when the safety system detects that the patient is trying to leave the bed. The patient monitoring system can send an alert to the care provider and/or sound an alarm if the patient tries to leave the bed and a care provider is not present with the patient.

17 Claims, 4 Drawing Sheets

(56) References Cited

U.S. PATENT DOCUMENTS

| | | |
|---|---|---|
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,844,488 A * | 12/1998 | Musick .................. 340/573.4 |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,019 A | 5/2000 | Scott |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |

(56) References Cited

U.S. PATENT DOCUMENTS

| | | |
|---|---|---|
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,734,476 B2 * | 6/2010 | Wildman et al. ............ 705/2 |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |

(56) References Cited

U.S. PATENT DOCUMENTS

| | | | |
|---|---|---|---|
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 * | 5/2014 | Kiani ................ 340/573.7 |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 2008/0122616 A1 | 5/2008 | Warner et al. |
| 2009/0119843 A1 * | 5/2009 | Rodgers et al. ............ 5/611 |
| 2009/0260158 A1 | 10/2009 | Kazuno et al. |
| 2012/0025991 A1 | 2/2012 | O'Keefe et al. |

\* cited by examiner

PATIENT SAFETY SYSTEM WITH AUTOMATICALLY ADJUSTING BED

PRIORITY CLAIM TO RELATED PROVISIONAL APPLICATIONS

The present application is a continuation of U.S. application Ser. No. 13/277,145, filed Oct. 19, 2011, entitled "Patient Safety System With Automatically Adjusting Bed," which claims priority benefit under 35 U.S.C. §119(e) to U.S. Provisional Patent Application Ser. No. 61/405,097, filed Oct. 20, 2010, also entitled "Patient Safety System With Automatically Adjusting Bed." The present application incorporates the foregoing disclosure herein by reference.

BACKGROUND OF THE INVENTION

Patient safety systems are commonly found in medical and geriatric facilities, and often incorporate adjustable beds. Generally, these beds include a guard rail assembly which can be raised to prevent the patient from falling out of the bed. The guard rail can be lowered to allow the patient ingress and egress from the bed or to provide the care provider unobstructed access to the patient for treatment. The height of some beds can be adjusted to raise the patient to a proper level for treatment by the care provider and the bed can also be lowered for easier patient ingress and egress.

There have been numerous instances in which patients have fallen out of bed, even with the presence of guard rails. In some instances, the care provider may forget to return the guard rails to the raised position after treatment, allowing the patient to roll off the bed. Even where the guard rails are returned to the raised position, a restless patient can easily climb over top of the guard rails and potentially fall to the floor. The situation can be exacerbated in some instances involving height adjustable beds, where the bed height may be inadvertently left in the raised position, resulting in the patient falling from a higher distance off the raised bed. Injuries from these falls can not only be traumatic but also catastrophic, possibly resulting in death.

SUMMARY OF THE INVENTION

Aspects of the present disclosure include a bed with safety features to reduce the risk of accidental patient injury. In an embodiment, a raisable patient bed is described which is configured to automatically lower from a raised position when certain criteria are met. For example, the criteria can include when a patient's movements indicate that a patient is attempting to leave the bed or when a guard rail is lowered by a patient. Other criteria can also be used as described further herein. In an embodiment, an alarm feature can also be used to alert care providers that a patient is attempting to leave the bed. In an embodiment, both an alarm feature and an automatically lowering feature can be used in conjunction with each other.

Thus, in accordance with at least one of the embodiments disclosed herein, a patient safety system can comprise an adjustable bed adjustable between at least a lowered position and a raised position. A first sensor can be configured to detect the presence of a care provider and a second sensor can be configured to detect when a patient is trying to leave the bed. The adjustable bed can be configured to automatically adjust to the lowered position when the first sensor indicates that a care provider is not present and the second sensor indicates that a patient is trying to leave the bed.

In some embodiments, the patient safety system can also include at least one movable guard rail on the lateral side of the bed, the guard rail movable between a lowered configuration and a raised configuration, wherein in the raised configuration the guard rail obstructs the patient from falling off the bed. The bed can adjust to where the guard rails are in a raised configuration when the first sensor indicates that a care provider is not present and the second sensor indicates that a patient is trying to leave the bed.

In some embodiments, the patient safety system can further comprise an alarm linked to the first and second sensors that is triggered when the first sensor does not detect the care provider and the second sensor detects that a patient is trying to leave the bed.

In accordance with another embodiment disclosed herein, the patient safety system can comprise an adjustable bed adjustable between at least a first position and a second position, and a first sensor configured to determine the presence of a care provider near the patient. The adjustable bed can be configured to automatically adjust from the first position to the second position when the presence of a care provider is no longer detected.

In some embodiments, the patient safety system can comprises at least one movable guard rail on the lateral side of the bed that moves from a lowered configuration to a raised configuration when the presence of a care provider is no longer detected. In some embodiments, the patient safety system can comprise a height adjustment that moves from a raised position to a lowered position when the presence of a care provider is no longer detected.

In some embodiments, the adjustable bed can wait a predetermined period of time after the presence of a care provider is no longer detected before adjusting from the first position to the second position.

The patient safety system can further comprise a monitoring station or a pager that displays an alert when the first sensor does not detect the care provider and the second sensor detects that a patient is trying to leave the bed.

In a method of monitoring a patient in a bed, the method can comprise the steps of determining whether a care provider is near the patient and adjusting the bed to a predetermined configuration when the care provider is determined not to be near the patient. In some embodiments, the method can further comprise determining whether a patient is trying to leave the bed and sounding an alarm and adjusting the bed to a predetermined configuration when the patient is determined to be trying to leave the bed and the care provider is determined to have left the patient.

BRIEF DESCRIPTION OF THE DRAWINGS

Specific embodiments and modifications thereof will become apparent to those skilled in the art from the detailed description herein having reference to the figures that follow, of which.

DETAILED DESCRIPTION OF SPECIFIC EMBODIMENTS

A patient safety system including safety beds that can automatically adjust to a safe default configuration and a patient monitoring system for detecting the movement of a patient are disclosed herein. Such safety systems can be particularly advantageous to substantially prevent or reduce the risk of injuries to patients from falls off beds.

A patient safety system having desirable features and advantages will now be described with reference to the figures. Although the following description is provided in the context of an example patient safety system, it should be understood that the disclosure is not limited by the examples or claims. None of the structures, steps, or other features disclosed herein are essential or indispensible; any can be omitted or substituted by an equivalent.

Certain terms are used herein, such as "higher," "lower," "lateral" and the like, to assist in providing a frame of reference. These terms should not be construed as limiting the present disclosure and should be recognized as having their ordinary meaning. Furthermore, the term "computer" used herein should be broadly interpreted as any device or group of components that can accept input information from a user input or from another source such as, for example, another computer, process the information, and/or output information, such as to another device or to a display screen.

SAFETY BED

Figure 1:
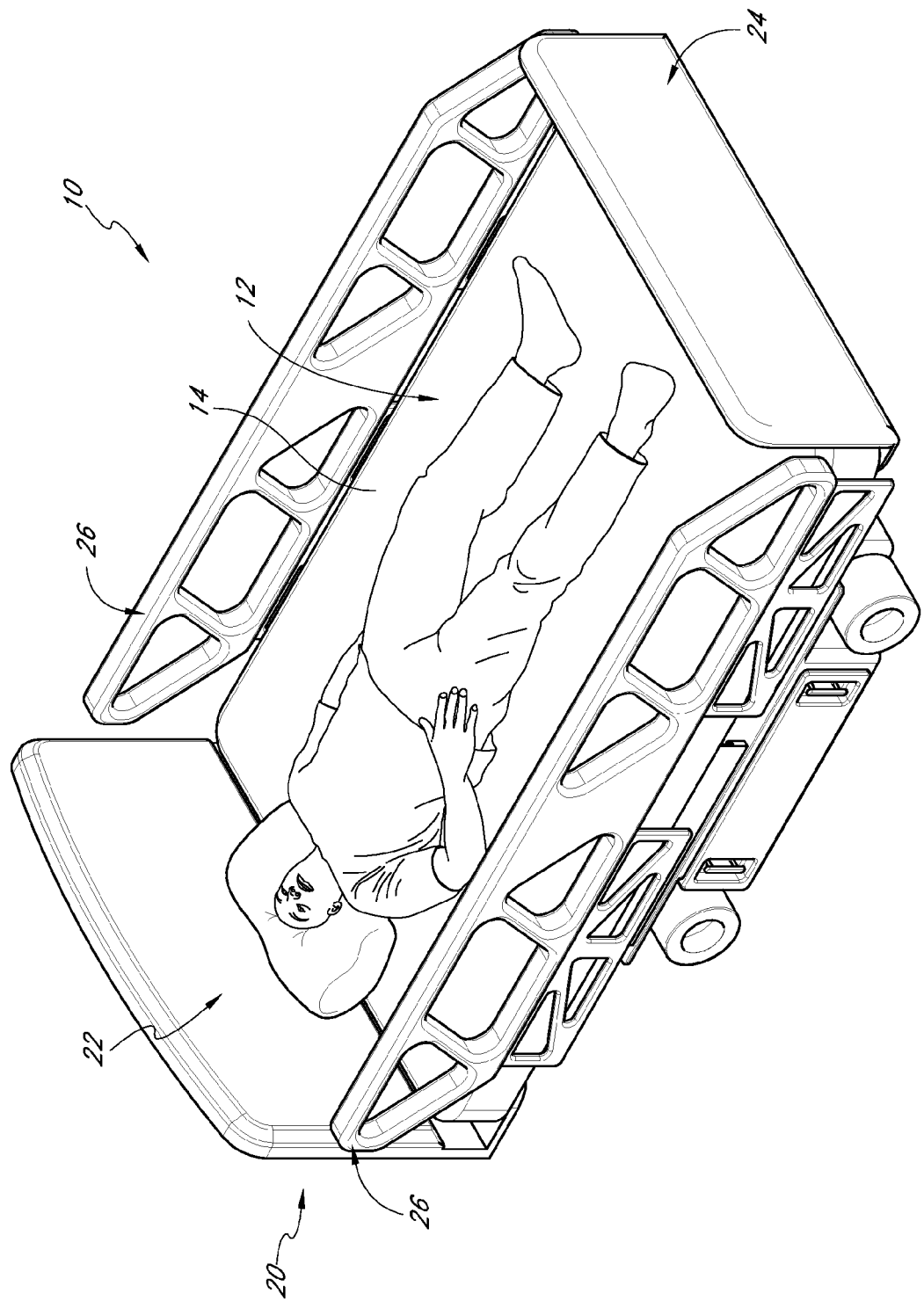
FIG. 1 is a schematic top perspective view of an embodiment of a safety bed illustrated in a flat, lowered position and the guard rails in a raised configuration.

Referring to FIG. 1, a safety bed 10 is illustrated having a mattress 12 and a frame 20. The frame 20 can include a headboard 22 at one side of the bed, a footboard 24 at the opposite side of the bed, and a set of guard rails 26 on each lateral side of the bed interposed between the headboard 22 and the footboard 24. Each of the headboard 22, footboard 24 and guard rails 26 extend above a top surface 14 of the mattress 12 to form a perimeter around the mattress 12 for retention of the patient on the bed 10.

The guard rails 26 can be substantially planar members sized to obstruct substantially the entire lateral sides between the footboard 24 and the headboard 22. In some embodiments, the guard rails 26 can comprise more than one piece on each side of the bed. In some embodiments, the guard rails 26 can be planar members. In other embodiments, the guard rails can be a frame structure, as illustrated in FIG. 1. Each of the guard rails 26 can include a set of transparent windows made from Plexiglas, polycarbonate, or other suitable material, that can allow a care provider to monitor a patient through the window without having to look over the guard rail 64.

Figure 2:
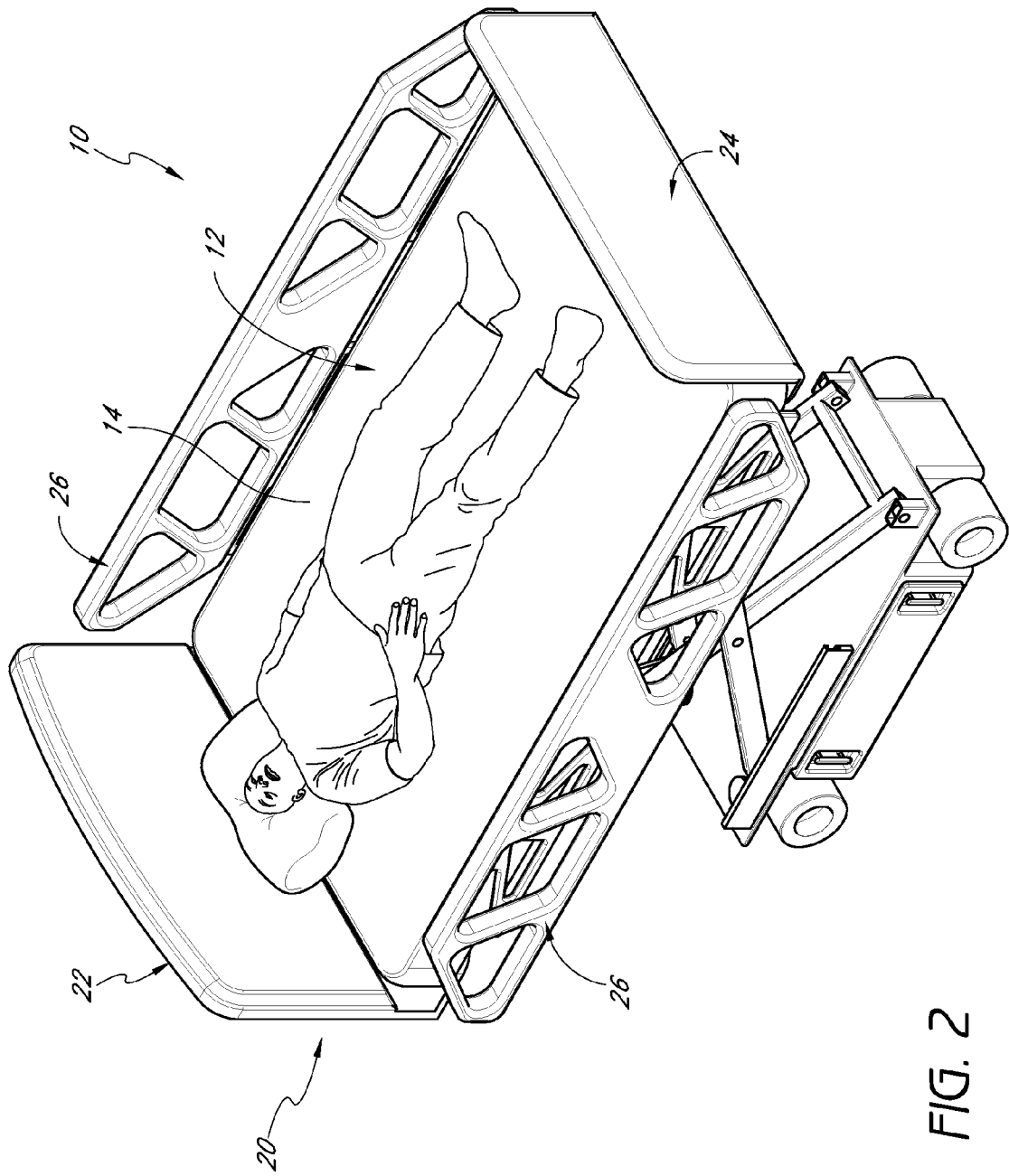
FIG. 2 is a schematic top perspective view of an embodiment of a safety bed illustrated in a flat, raised position and the guard rails in a lowered configuration.

As illustrated in FIG. 2, the guard rail 26 can have a lowered configuration wherein the guard rail 26 is moved downward to provide improved access to the patient. In some embodiments, the guard rail 26 can be hinged at the lower end such that it can rotate about the lower edge between a raised configuration, such as shown in FIG. 1, and a lowered configuration, such as shown in FIG. 2. In other embodiments, the guard rail 26 can slide along a channel from a raised configuration to a lowered configuration. In still other embodiments, the guard rail 26 can have double armed hinges that allow the guard rail 26 to swing from a raised configuration to a lowered configuration while remaining in the same orientation. In some embodiments, the guard rail 26 can be held in the raised and/or lowered configuration by detents, hooks, tabs or other known securement devices. In some embodiments, switches or sensors can be disposed on or adjacent the guard rail 26, so that a computer or processor can detect the position of the guard rails 26. When the guard rail 26 is in the raised configuration, the patient is constrained from rolling out of the bed 10. In the lowered configuration, the guard rails 26 are out of the way so that the care provider can have improved access to the patient.

In some embodiments, the headboard 22 and/or footboard 24 can be configured to move downward to provide improved access to the patient, similar to the guard rail 26 described above. The features and methods described for the lowering of the guard rail 26 can be applicable to the headboard 22 and/or footboard 24 to move it into a lowered configuration.

With continued reference to FIG. 2, in some embodiments, the safety bed 10 can be in a raised position. In the raised position, a patient lying on the mattress 12 can be more easily attended to by a care provider without having to bend down. The patient can still be safely constrained in the safety bed 10 where the guard rail 64 is in the raised configuration. If the care provider needs better access to the patient, the guard rail 26 can be moved to a lowered configuration, as illustrated in FIG. 2.

In some embodiments, the mattress 12 can be adjusted to raise the patient's head, raise the patient's legs, or tilt the patient's whole body. In some situations, it can be medically advantageous to raise the patient's head or legs, such as to assist blood circulation, assist respiratory function, or improve delivery of medication to the patient.

Referring to FIG. 1, the safety bed 10 can be changed to a lowered position. With the safety bed 10 in the lowered position, it is easier for the patient to get on and off the bed. Furthermore, the lowered position can be safer because the safety bed 10 is advantageously closer to the ground in case the patient falls from the bed. In the lowered position, a care provider can still access the patient, with the guard rails 26 in either the lowered or raised configurations.

In some situations, the care provider may forget or otherwise neglect to move the guard rail 26 to a raised configuration or lower the bed 10 to a lowered position or return the mattress to a flat configuration after treating the patient. If the care provider fails to return the guard rails 26 to a raised configuration, then the risk of the patient rolling off the bed 10 is increased. Even where the guard rails 26 are returned to a raised configuration, the patient can still climb over the guard rail 26 and off the bed. Therefore, if the care provider fails to return the bed 10 to a lowered position, then the risk of the patient falling from a raised height is increased, which can result in severe injuries. Furthermore, if the mattress is left in a tilted or angled configuration, it may be easier for the patient to roll off the bed or climb over the guard rails 26. If the care provider fails to return the guard rails 26 to the raised configuration and the bed to the flat, lowered position, then the patient's risk of injury from rolling off the bed at a raised height is increased.

Therefore, an aspect of the present disclosure is to provide a safety bed 10 that automatically returns the bed 10 to a default safe configuration after the patient has been treated. In some embodiments, the default safe configuration is where the safety bed 10 is in a lowered height position. In some embodiments, the default safe configuration is where the guard rails 26 are in a raised configuration. Furthermore, the default safe configuration is where the mattress 12 is in a generally flat configuration. In preferred embodiments, the default safe configuration is where the bed 10 is in a lowered height position and the guard rails 26 are in a raised configuration and the mattress 12 is generally flat. In some embodiments, the default safe position can be specified by the care provider. For example, the care provider may need to keep the head of the mattress 12 tilted up to help treatment of the patient. In this case, the care provider can define the default safe position where the safety bed 10 is in the lowered position and the guard rails 26 are in the raised configuration, with the head of the mattress 12 tilted up.

In some embodiments, a sensor 16 can be placed on the safety bed 10 or in the patient's room to detect when a care provider is present in the room. The signals can be emitted by a device attached to the care provider. In some embodiments, the care provider can wear a Radio Frequency Identification (RFID) tag that transmits a signal to the sensor 16 to notify a computer or processor of the care provider's presence. In some embodiments, other signal types can be used to indicate when a care provider is present, such as Bluetooth, cellphone signals, or other types of signals known in the art. When the care provider leaves the room, the signal is no longer present and the computer can send a signal to prompt the safety bed 10 to return to the default safe configuration. Therefore, if the care provider forgets or fails to return the bed 10 to the default safe configuration before leaving the patient's room, then the safety bed 10 can automatically return to the default safe configuration to help avert patient injuries from falls. In an embodiment, when the care provider leaves the room, the safety bed does not return to the default safety position immediately, but waits until patient motion is sensed which indicate the patient may be attempting to get off the bed.

In some embodiments, the safety bed 10 can wait a predetermined period of time after a care provider leaves the room before returning to the default safe configuration. For example, when the sensor 16 no longer detects the presence of the care provider, a timer can activate and the safety bed 10 can return to the default safe configuration at the end of the timer countdown. The predetermined amount of time can be adjustable and set by the care provider, or the time can be preset during manufacture of the bed. The amount of wait time can be at least approximately 5 seconds and/or less than or equal to approximately 30 minutes. In some embodiments, the amount of wait time can be at least approximately 15 seconds and/or less than or equal to approximately 15 minutes. Preferably, the amount of wait time can be at least approximately 30 seconds and/or less than or equal to approximately 5 minutes. In some embodiments, the timer can be overridden and the safety bed 10 can immediately return to the default safe configuration, such as when the patient monitoring system detects that the patient is trying to leave the bed. Monitoring of patient movements is described in greater detail below.

In some embodiments, other types of sensors, such as motion sensors or heat sensors, can detect movement or heat around the patient's bed to identify when a care provider is present. These types of sensors can advantageously be used without a transmitter or identification device worn by the care provider.

Some embodiments of the safety bed 10 can include a timer in addition to, or instead of, the sensors. The care provider can place the bed 10 in position for treating the patient. A timer can be automatically, or manually set so that the bed 10 returns to the default safe configuration after a set period of time. In some embodiments, an alarm can sound when the timer is nearing the end of its set time, so that the care provider can reset or add more time to the timer, if desired. If the care provider forgets to return the safety bed 10 to the default safe configuration, then the bed 10 will automatically return to the default safe configuration once the timer has run out.

In some embodiments, an alarm or voice notification can sound prior to and during the bed's movement to the default safe configuration to alert the patient and care providers of the automatic movement of the bed 10. For example, a recorded voice can alert the patient to remain calm and remain still while the bed 10 moves to the default safe configuration. In some embodiments, an alarm or notification can be transmitted to the care provider at a monitoring station 36 or through a pager system, as described below, to notify the care provider of the automatic movement of the bed 10.

PATIENT MONITORING

Figure 3:
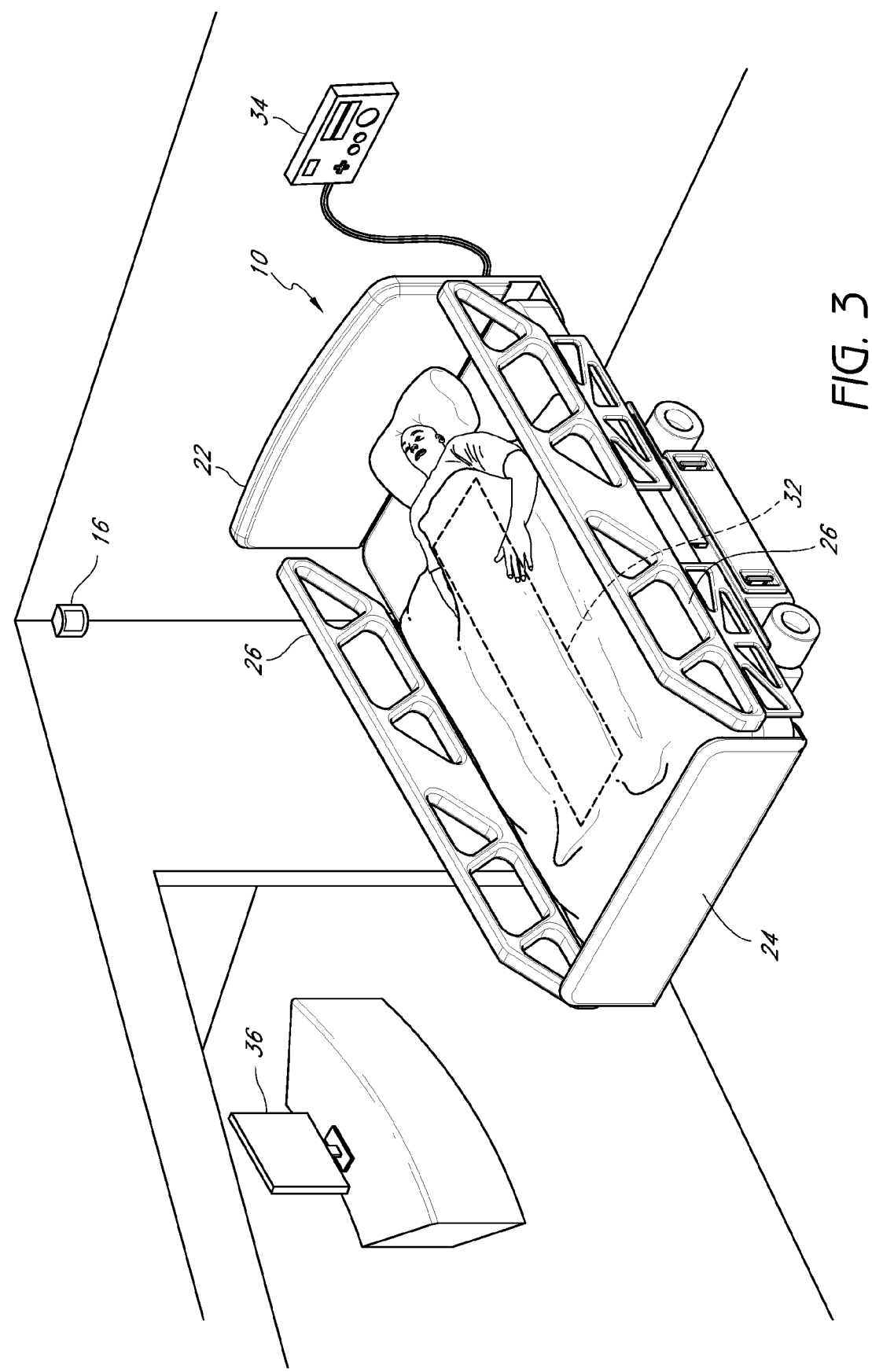
FIG. 3 is a schematic top perspective view of a patient room illustrating an embodiment of a patient safety system.

In some embodiments, a patient monitoring system can be used in conjunction with the safety bed 10. With reference to FIG. 3, the patient monitoring system can include a bed sensor 32 which can be positioned on or about the patient's bed. In some embodiments, the patient monitoring system can include a monitoring station 36 that displays the status of the patient.

Although any type of bed sensor 32 can be used with the patient monitoring system, bed sensors 32 having ribbon switches are particularly envisioned. For example, a ribbon switch can be used which has contacts that are held closed when a patient is properly positioned on the bed. When the patient's weight is present on the mattress, the ribbon switches are sufficiently compressed so that the ribbon contacts therein are electrically connected. If the patient moves their weight off of the sensor for more than a momentary delay, a computer 34 can recognize the open contacts of the switch. A delay circuit can be included in the bed sensor 32 to provide a delay so that momentary opening of the ribbon switch contacts due to a patient shifting positions, will not set off an alarm. In some embodiments, the bed sensor 32 can have ribbon switches that are disposed around the perimeter edge of the mattress. When the edge ribbon switches are activated, a signal can be transmitted to the computer 34 to report that the patient is trying to leave the bed 10. Other sensors can also be used with the present disclosure.

When the bed sensor 32 detects the patient's movements and determines that the patient is trying to leave the bed 10, the computer 34 can respond accordingly. In some embodiments, a signal can be sent to a light and/or alarm which can be positioned on the bed or in the patient's room to alert the care provider. A signal can be transmitted to the monitoring station 36 to alert the care provider. In some embodiments, when the computer 34 determines that the patient is trying to leave the bed, the computer can send commands to the bed 10 to place the bed in the default safe configuration, as described above, to reduce the risk of injury to the patient. As mentioned previously, an alarm or voice notification can sound prior to and during the movement of the bed 10 to the default safe configuration to help diminish any risk of injury to the patient or care provider during the transformation of the bed 10.

In some embodiments, the patient monitoring system can include an override switch so that the patient can be removed or repositioned on the bed without triggering the alarm system. In preferred embodiments, the override switch is positioned such that the care provider can access the switch, but is out of reach of the patient. In some embodiments, a timer can be connected to the override switch to turn off the override switch automatically after a predetermined period, to account for situations where the care provider may forget to turn off the override switch. In some embodiments, the override switch can be integrated with the sensor 16 that detects when the care provider is present in the room. The override switch can be activated when the care provider is in the patient's room and deactivated when the care provider leaves the room. In some embodiments, the presence of a patient care provider acts as an override switch such that the bed will not automatically move when a caregiver is present.

Most health care facilities have a patient monitoring system already in existence, which permits a patient to call the care provider and includes a light positioned over the patient's door and/or a monitoring station to alert the care provider of the need for attention. In these facilities, the safety bed 10 can be integrated into the existing patient monitoring system.

In some embodiments, the patient monitoring system can include a paging system that transmits a radio frequency signal, or other over-the-air (OTA) signal, to a monitoring station. The transmitter for a particular patient monitoring system can provide a discreet signal so that each signal can be discernable by the monitoring station to identify the patient from which an alarm signal originates. Some embodiments of the paging system can include personal pagers carried by the care providers that receive signals alerting the care provider of the status of the patient. Each patient can be assigned a discreet frequency such that only select care providers are alerted for a specific patient.

OPERATION OF SAFETY SYSTEM

Figure 4:
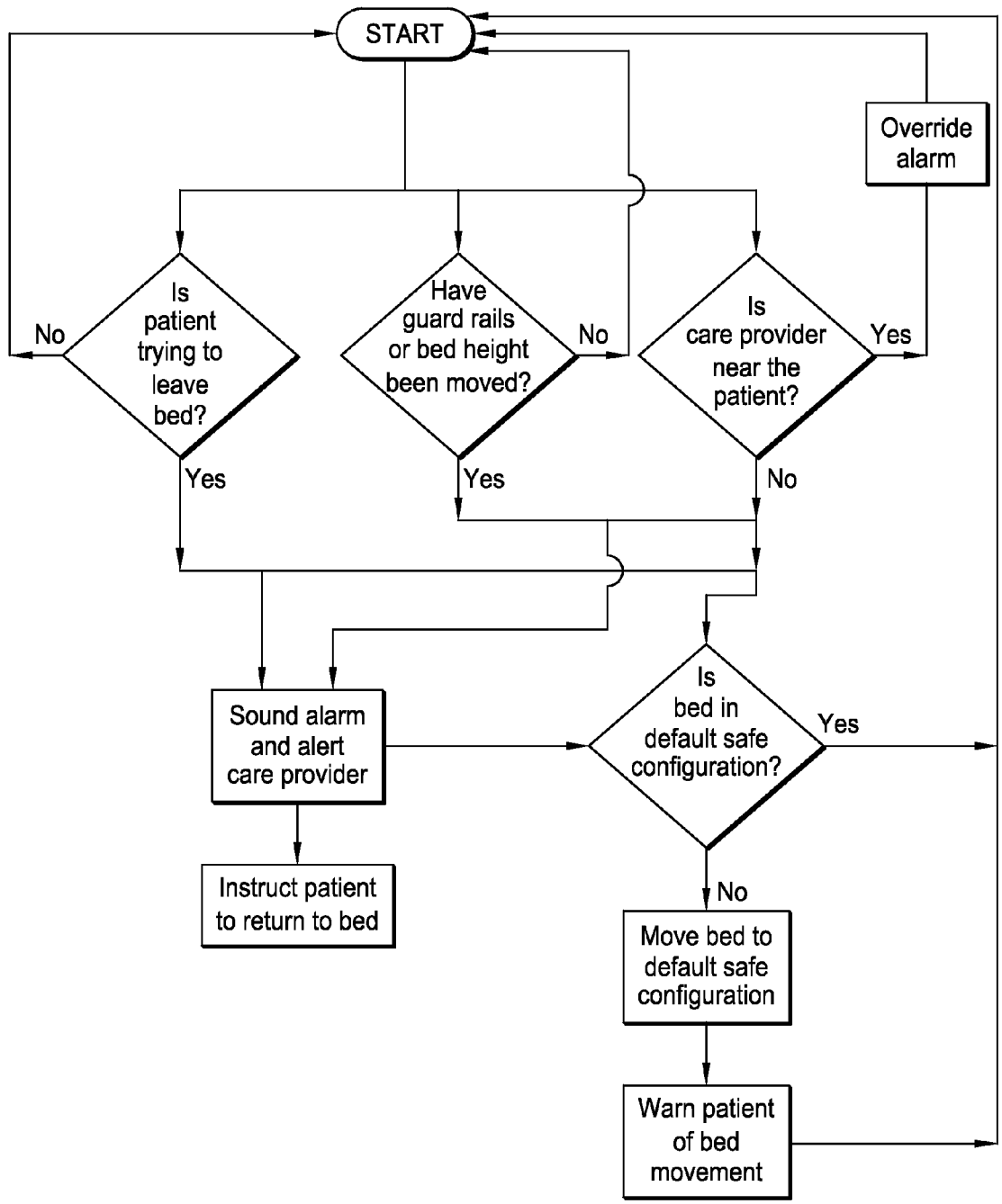
FIG. 4 is a flowchart of the operation of an embodiment of a patient safety system.

In the operation of the safety bed 10 and patient monitoring system described thus far, reference is made to FIG. 4. When a care provider enters a patient's room, a sensor 16 detects the presence of the care provider. The care provider can adjust the safety bed 10 to a raised position and move the guard rails 26 to a lowered configuration for improved access to the patient. In some embodiments, an alarm that sounds when the guard rails 26 are lowered or when the bed 10 is raised can be deactivated or overridden by the care provider. In some embodiments, the alarm can be automatically deactivated when the care provider's presence is detected by the sensor 16. When the sensor 16 no longer detects the care provider's presence in the room, the safety bed 10 can automatically return to its default safe configuration; e.g. the bed 10 is changed to a flat, lowered position and the guard rails 26 are moved to a raised configuration. In some embodiments, the safety bed 10 can emit an alarm or verbal warning to alert the patient that the bed is moving or about to move. In some embodiments, the safety bed 10 can wait a predetermined period of time after the care provider leaves the room before returning to its default safe configuration, as described above.

When the system does not detect a care provider in the patient's room, the patient monitoring system can supervise the patient. When a patient is positioned in the bed 10, the patient's weight can trigger bed sensors 32 disposed on or under the mattress 12, which informs the computer that the bed 10 is occupied. If the patient's weight is removed from the mattress 12, the bed sensors 32 inform the computer 34 that the patient is no longer in proper position in bed. The computer 34, in turn, can send an alert signal to the monitoring station 36 and audible/visible alarm. The monitoring station 36 can have a visual display readout that identifies the location or room where the bed sensors 32 have detected undesired patient movement. In some embodiments, the audible/visible alarm can provide a warning within the normal audible range of a patient to let the patient know that he/she has caused an alarm by his movement, which in many cases will remind the patient that he/she is exceeding the desired movement range and thereby encourage the patient to return to the desired position on the bed 10. One such audible alarm can be a voice message such as: "Please return to your bed," or similar message, so that the patient will be encouraged to return to bed 10. In some embodiments, the computer 34 can send a signal to trigger a remote alarm, for example in the hospital corridors or care provider station. In some embodiments, the computer 34 can send a signal to a transmitter to sends a discreet frequency signal to a particular monitoring station 36 or particular pager for a specific care provider. In some embodiments, the safety bed 10 can return to the default safe configuration when the patient monitoring system detects that the patient is trying to leave the bed 10.

A power supply can provide power to all components of the patient safety system described above for simpler set-up where electrical outlets are not available, such as remote or undeveloped areas. The independent power supply can simplify integration of the patient safety system into existing systems, by eliminating the need to tap into the existing system's power supply. Even when the patient safety system is connected to the local power system, the independent power supply can provide back-up power in case of local power outages.

Although certain embodiments, features, and examples have been described herein, it will be understood by those skilled in the art that many aspects of the methods and devices illustrated and described in the present disclosure may be differently combined and/or modified to form still further embodiments. For example, any one feature of the safety bed system described above can be used alone or with other components without departing from the spirit of the present invention. Additionally, it will be recognized that the methods described herein may be practiced in different sequences, and/or with additional devices as desired. Such alternative embodiments and/or uses of the methods and devices described above and obvious modifications and equivalents thereof are intended to be included within the scope of the present invention. Thus, it is intended that the scope of the present invention should not be limited by the particular embodiments described above, but should be determined only by a fair reading of the claims that follow.

What is claimed is:

1. A patient safety system comprising:
    an adjustable bed adjustable between at least a lowered position and a raised position, the adjustable bed including a mattress,
    a first sensor configured to detect the presence of a care provider; and
    a second sensor configured to detect when a patient is trying to leave the bed,
    wherein the second sensor is at least one ribbon sensor disposed around a perimeter edge of the mattress;
    wherein the mattress can be adjusted to an angled configuration and a generally flat configuration;
    wherein the adjustable bed is configured to automatically adjust to the lowered position when the first sensor indicates that a care provider is not present and the second sensor indicates that a patient is trying to leave the bed; and
    wherein the bed adjusts to where the mattress is in the generally flat configuration when the first sensor indicates that a care provider is not present and the second sensor indicates that a patient is trying to leave the bed.

2. The patient safety system of claim 1, further comprising:
    at least one movable guard rail on a lateral side of the bed, the guard rail movable between a lowered configuration and a raised configuration, wherein in the raised configuration the guard rail obstructs the patient from falling off the bed;
    wherein the bed adjusts to where the guard rails are in a raised configuration when the first sensor indicates that a care provider is not present and the second sensor indicates that a patient is trying to leave the bed.

3. The patient safety system of claim 1, further comprising an alarm linked to the first and second sensors, wherein the alarm is triggered when the first sensor does not detect the care provider and the second sensor detects that a patient is trying to leave the bed.

4. A patient safety system comprising:
an adjustable bed adjustable between at least a first position and a second position, wherein the adjustable bed includes a mattress and at least one ribbon sensor disposed around a periphery edge of the mattress;
a first sensor configured to determine the presence of a care provider near the patient;
wherein the adjustable bed is configured to automatically adjust from the first position to the second position when the presence of a care provider is no longer detected and the at least one ribbon sensor is activated;
wherein the adjustable bed comprises the mattress can be adjusted to an angled configuration and a generally flat configuration, wherein the first position comprises the mattress in the angled configuration and the second position comprises the mattress in the generally flat configuration.

5. The patient safety system of claim 4, wherein the patient safety system further comprises:
a second sensor configured to determine if a patient located in the bed is attempting to leave the bed; and
an alarm;
wherein the alarm is triggered when the first sensor detects that the care provider is not present and the second sensor detects that a patient is trying to leave the bed.

6. The patient safety system of claim 5, further comprising a monitoring station, wherein the monitoring station displays an alert when the first sensor does not detect the care provider and the second sensor detects that a patient is trying to leave the bed.

7. The patient safety system of claim 5, further comprising a pager carried by the care provider, wherein the pager displays an alert when the first sensor does not detect the care provider and the second sensor detects that a patient is trying to leave the bed.

8. The patient safety system of claim 4, wherein the adjustable bed comprises at least one movable guard rail on a lateral side of the bed, the guard rail movable between a lowered configuration and a raised configuration, wherein in the raised configuration the guard rail obstructs the patient from falling off the bed, wherein the first position comprises the guard rail in the lowered configuration and the second position comprises the guard rail in the raised configuration.

9. The patient safety system of claim 4, wherein the adjustable bed comprises a height adjustment, adjustable between a lowered position and a raised position, wherein the first position comprises the bed in the raised position and the second position comprises the bed in the lowered position.

10. The patient safety system of claim 4, wherein the adjustable bed waits a predetermined period of time after the presence of a care provider is no longer detected before adjusting from the first position to the second position.

11. The patient safety system of claim 10, wherein the predetermined period of time is at least 5 seconds and/or less than or equal to 30 minutes.

12. The patient safety system of claim 4, wherein the first sensor detects an identifier carried by the care provider.

13. The patient safety system of claim 12, wherein the identifier is a radio frequency identification tag.

14. A method of monitoring a patient in a bed, the method comprising the steps of:
determining whether a care provider is near the patient;
sensing movement of a patient toward the edge of the bed using at least one ribbon sensor disposed about a periphery edge of the bed; and
adjusting the bed to a predetermined configuration when the care provider is determined not to be near the patient and the ribbon sensor is activated;
wherein adjusting the bed further comprises adjusting the bed between an angled configuration and a generally flat configuration.

15. The method of monitoring a patient in a bed of claim 14, the method further comprising the steps of:
determining whether a patient is trying to leave the bed;
sounding an alarm and adjusting the bed to a predetermined configuration when the patient is determined to be trying to leave the bed and the care provider is determined to have left the patient.

16. The method of monitoring a patient in a bed of claim 14, wherein the predetermined configuration comprises where guard rails on lateral sides of the bed are in a raised configuration, the bed is in its lowest height position, and a laying surface of the bed is generally flat.

17. The method of monitoring a patient in a bed of claim 14, wherein the step of determining whether a care provider is near the patient comprises using a sensor that detects an identifier carried by the care provider.

* * * * *